(12) United States Patent
Shargian

(10) Patent No.: US 11,779,714 B1
(45) Date of Patent: Oct. 10, 2023

(54) PEDIATRIC RESPIRATORY THERAPY INHALER APPARATUS

(71) Applicant: BSD SAGI, LLC, New Orleans, LA (US)

(72) Inventor: Moshe Shargian, Metairie, LA (US)

(73) Assignee: BSD SAGI, LLC

( * ) Notice: Subject to any disclaimer, the term of this patent is extended or adjusted under 35 U.S.C. 154(b) by 415 days.

(21) Appl. No.: 16/991,677

(22) Filed: Aug. 12, 2020

Related U.S. Application Data

(60) Provisional application No. 63/062,706, filed on Aug. 7, 2020, provisional application No. 62/885,573, filed on Aug. 12, 2019.

(51) Int. Cl.
*A61M 15/00* (2006.01)

(52) U.S. Cl.
CPC ...... *A61M 15/0026* (2014.02); *A61M 15/009* (2013.01); *A61M 15/0086* (2013.01); *A61M 2240/00* (2013.01)

(58) Field of Classification Search
CPC ........ A61M 11/00–08; A61M 15/0026; A61M 15/0086; A61M 15/009; A61M 2240/00; B05B 17/00–085

USPC .................................................... 128/200.23
See application file for complete search history.

(56) References Cited

U.S. PATENT DOCUMENTS

| | | | | |
|---|---|---|---|---|
| 2005/0061318 | A1* | 3/2005 | Faram | A61M 16/0096 128/204.21 |
| 2014/0166029 | A1* | 6/2014 | Weigensberg | A24F 40/30 131/329 |
| 2019/0111223 | A1* | 4/2019 | Harrison | A61M 11/06 |

FOREIGN PATENT DOCUMENTS

| | | | | |
|---|---|---|---|---|
| CN | 210542749 U | * | 5/2020 | |
| WO | WO-2004096110 A2 | * | 11/2004 | A63B 23/18 |

* cited by examiner

*Primary Examiner* — Elliot S Ruddie
(74) *Attorney, Agent, or Firm* — ADAMSIP, LLC; James Adams; Stephen Thompson

(57) ABSTRACT

A flavored attachment can adhere to the mouthpiece of an inhaler or the like, wherein the attachment is designed so that it lasts for a sufficient duration to ensure the person taking the medicine has taken the proper dosage.

9 Claims, 22 Drawing Sheets

PEDIATRIC RESPIRATORY THERAPY INHALER APPARATUS

CROSS-REFERENCE TO RELATED APPLICATIONS

Priority of U.S. Provisional Patent Application Ser. No. 63/062,706, filed Aug. 7, 2020; and U.S. Provisional Patent Application Ser. No. 62/885,573, filed Aug. 12, 2019, each of which is hereby incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to pediatric inhalers use for respiration therapy wherein the patient inhales tiny droplets of a doctor prescribed pharmaceutical atomized by a compressor, tube and nebulizer that contains the prescribed pharmaceutical. More particularly, the present invention relates to a method and apparatus designed to increase the efficacy of pediatric inhalers that are designed for use with pharmaceuticals added to a reservoir of the inhaler by providing a candy or flavored (e.g., consumable) attachment which can be adhered to the mouthpiece of a pediatric inhaler so that the child will utilize the mouthpiece for the requisite time (e.g., as much as 15-20 minutes) to ensure proper dosage. Accordingly, the flavored attachment is designed to last long enough for the required dosage to be inhaled or consumed. In another embodiment, the present invention can comprise an inhaler wherein the mouthpiece is provided with the candy attachment in a single unit.

2. Related Information

Pediatric inhaler devices are known and commercially available (e.g., Vios® from Pari Respiratory Equipment, Inc. (www.pari.com) of Midlothian, VA). Such pediatric inhaler devices provide a mouthpiece for the child to hold in his or her mouth, tubing to connect to a machine that has a compressor, a nebulizer or nebulizer cup having a chamber defining a reservoir for holding a selected pharmaceutical (e.g., Albuterol or budesonide), an air inlet connector providing an interface between the tubing and the nebulizer, and a connector that interfaces the nebulizer and mouthpiece (e.g., a fitting such as a tee fitting).

The following U.S. Patents are incorporated herein by reference: U.S. Pat. Nos. 6,702,997; 8,671,934; 9,452,270; and 9,452,274; U.S. Patent Application Publication Nos.: 2009/0062855; 2012/0190999; 2014/0202457; 2014/0207016; 2014/0261400; 2018/0192693; and 2019/0111223; and International Patent Publication No. WO 2017007489. Additionally, the following website, related to U.S. Patent Application Publication No. 2019/0111223, is incorporated herein by reference.

BRIEF SUMMARY OF THE INVENTION

The apparatus of the present invention is an inhaler attachment for inhaled pharmaceutical for patients, especially children, which has candy or a flavored, consumable coating on the mouthpiece (or, alternatively, a strip of candy or flavored, consumable coating with an adhesive that can be applied to the mouthpiece of the inhaler). The candy should preferably last long enough to ensure that the child will keep the mouthpiece in his or her mouth long enough for a proper dose of medicine to be consumed (for example, at least about 15 minutes), but can last between 1 and 15 minutes, and up to 15 minutes (or even longer if the proper dosage requires more time). The duration that the candy or flavored, consumable coating can last can vary depending on the dosage time required. The attachment of candy on the mouthpiece will aid in solving the problem often encountered when children are reluctant to take medicine or consume the full amount of medicine needed through a mouthpiece. That is part of a nebulizer or nebulizer cup connected to an air compressor.

The present invention comprises a candy adhesive or the like, such as a flavored, consumable coating which can be applied to the mouthpiece of an inhaler or on a nebulizer or similar medical aeration therapy devices. Preferably, the present invention can be used on mouthpieces for nebulizers, chambers, spacers, puffers, masks, inhalers, respiratory devices, and respiratory tubing, such as those used in hospital settings. Preferably, the device can be made in different sizes for different age children. For example, there may be small, medium, or large sizes available, or some other suitable size scale. In tests, gummy bear type candy and Nutella have been used. The apparatus comprises a candy and can be different types of materials, such as hard candy, jelly candy, frozen candy, dissolvable candy (such as that used in LISTERINE® strips), or other suitable candy material. The apparatus can comprise a separate adhesive layer which is utilized to adhere the candy to the mouthpiece of an inhaler, for example. The candy may be adhered to the inhaler where the mouthpiece is located. A preferred embodiment of the present invention comprises an edible adhesive layer. In certain embodiments, the adhesive layer can be part of, and the same material as, candy. The adhesive can be included in the candy or even added to it later. Various candies or flavors can be utilized. The candy layer can be of various thicknesses depending on the desired length of treatment. The apparatus of the present invention can be provided as an attachment to attach to an inhaler, or as part of the inhaler in a single device.

The apparatus can comprise a candy surrounding a sleeve which sleeve can then be placed onto an inhaler. The sleeve can be sold already assembled on the inhaler. The sleeve can be made of elastic material, for example. An advantage of the embodiments which is comprise the sleeve is that it can easily be attached and detached from a mouthpiece.

The present invention presents a candy attachment for a mouthpiece which is used to distribute medicine to a patient as part of aeration therapy. In one embodiment, the candy is able to slip into the inhaler tube, wherein the air flow with the medicine travels through the candy. Similarly, the candy acts as an inhaler tube and is connected into the inhaler and the air flow is able to flow out of the candy.

In another embodiment and related embodiments, the candy or similar flavored substance is locked onto the outside of the nebulizer using a locking device (e.g., silicone), and the candy or similar flavored substance is shaped such that it can be locked in place using the locking device, but consumed by the child while the child receives treatment via the nebulizer/inhaler. Other variations could include a lollipop shaped candy with a locking mechanism for the lollipop handle.

In one embodiment, there is a safety net or guard on each candy to prevent swallowing or aspiration by the patient. The safety net can be placed on the device to cover and protect the user, but it is preferably on each candy piece in embodiments where the candy is separate from the device. The safety net can be mesh and made of silicone, plastic, or other suitable material. In some embodiments, the safety net is also made of candy or food substance. Alternatively, there could be a slide mechanism similar to a pod container on a dishwasher, wherein the safety net surrounds the candy and is anchored by a rail sliding to the device.

Preferably, the candy is available in various shapes, bumps, stripes, spikes or other suitable shapes, some of which are shown in the figures. These shapes can also include cartoon characters, animals, logos, or other desirable designs (not shown). Additionally, the candy can be in a sponge-type shape and form that allows the treat to be absorbed in different levels of liquid types and concentrations. In some embodiments, there are provided different control mechanisms for treatment level, duration and timing, for example a button, spring, speed stick, injection, or other suitable mechanism.

In another embodiment of the present invention, molds are provided to enable a patient to make their own candy shapes for home medicine applications.

The present invention also includes flavor strips that can be wrapped around the device.

The mouthpiece of the present invention is preferably a universal size which can fit on any inhaler; alternatively, it can be provided in sufficient sizes to fit on any commercially available inhaler. For example, the dimensions can be as follows: ID—1-3.5 cm, preferably 1.5-2.5 cm, most preferably 2-2.5 cm; OD—1.5-3.8 cm, preferably 1.7-2.8 cm, most preferably 2-2.7 cm; length—5-15 cm, preferably 6.5-12.5 cm, most preferably 6.5-10.5 cm.

The flavorings of the candy (or other flavored substance on/in the mouthpiece) can be any appropriate flavoring, such as disclosed in US Patent Publication No. US 2007/0031343 A1, incorporated herein by reference. Also, one could flavor the medicine of the inhalant as disclosed in US Patent Publication No. US 2007/0031343 A1.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

Figure 1:
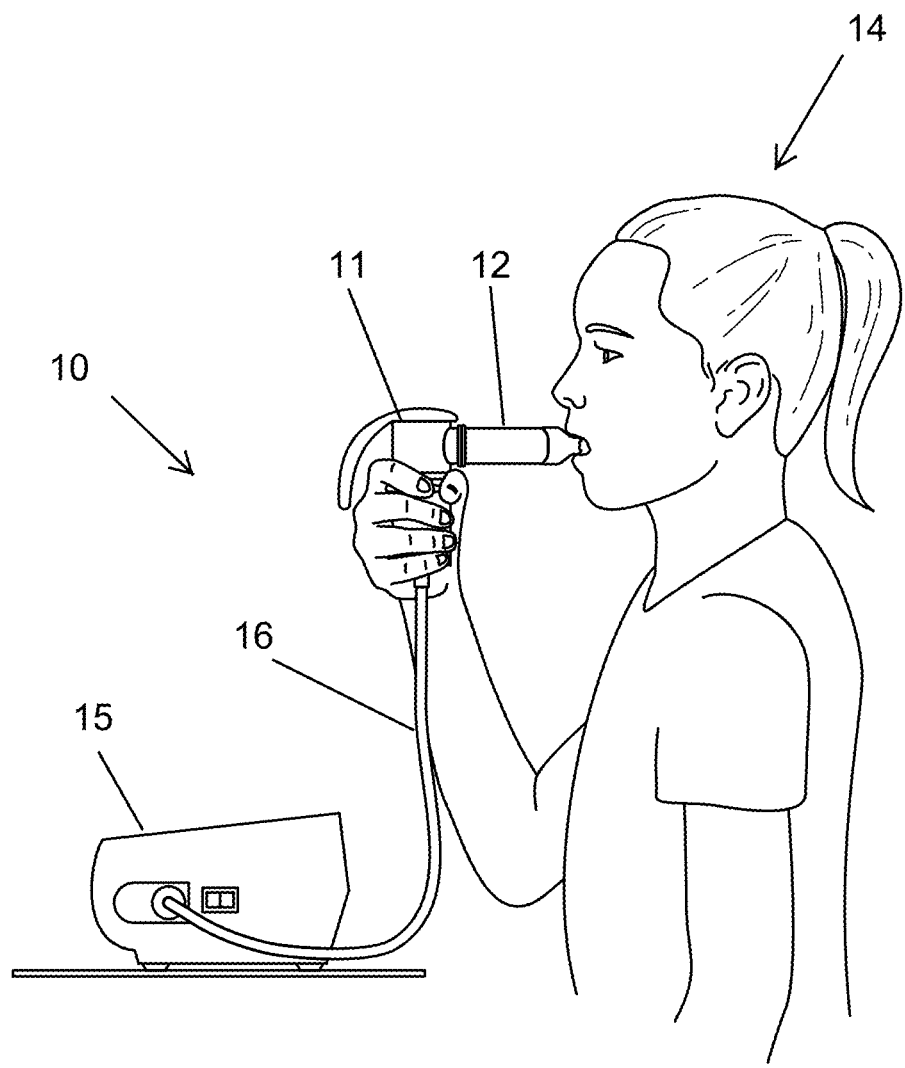
FIG. 1 is a perspective view of a preferred embodiment of the apparatus of the present invention.

FIG. 1 is a schematic diagram of a pediatric inhaler 10 in one embodiment of the method and apparatus of the present invention wherein a nebulizer or nebulizer cup 11 having a mouthpiece 12 is fitted with a candy item, layer, coating or candy fitment 13 (see FIGS. 2-3, 5-7, 11, 14 and 24-26) that provides flavor to child 14. Nebulizer cup 11 is provided with air from compressor 15 and tubing section 16. A nebulizer cup with a mouthpiece tubing section and compressor is commercially available and sold under the trademark Vios and from Pari Respiratory Equipment, Inc. of Midlothian, VA. The nebulizer cup 11 turns a liquid medicine component contained in a reservoir or medicine container (not shown) into an aerosol mist. For respiration or aerosol therapy, repeated inhaling/exhaling is required while simultaneously holding the mouthpiece in a user's mouth and while the user's lips seal against the mouthpiece. For very young users, children or toddlers concentration can be low so that the user does not continuously inhale/exhale for a doctor prescribed time interval that can be about 5-15 minutes or more. The pharmaceutical in the reservoir or container can be albuterol, budesonide or other drug that is doctor prescribed for respiratory or aerosol therapy used to treat patients having asthma, pneumonia, bronchitis, bronchiolitis, chronic obstructive pulmonary disease (COPD), and any other condition affecting air flow in the lungs.

Figure 18:
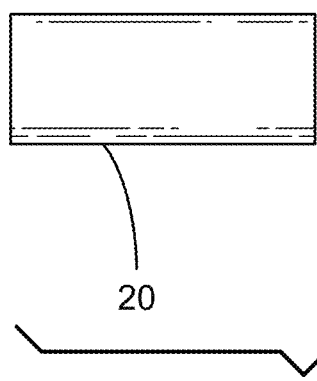
FIG. 18 is an exploded side view of a preferred embodiment of the apparatus of the present invention.
Figure 19:
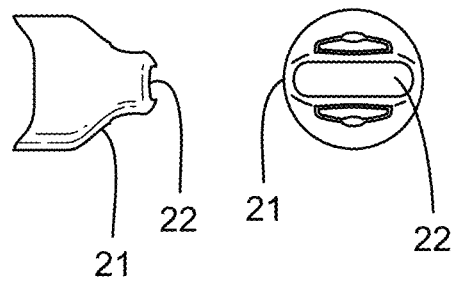
FIG. 19 is a fragmentary end view of a preferred embodiment of the apparatus of the present invention.
Figure 20:
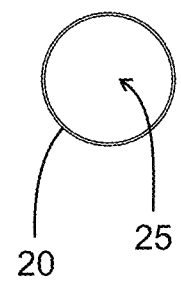
FIG. 20 is a fragmentary end view of a preferred embodiment of the apparatus of the present invention.
Figure 21:
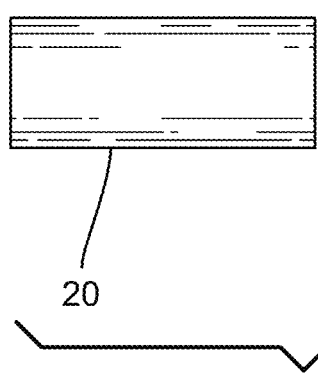
FIG. 21 is an exploded side view of a preferred embodiment of the apparatus of the present invention.
Figure 22:
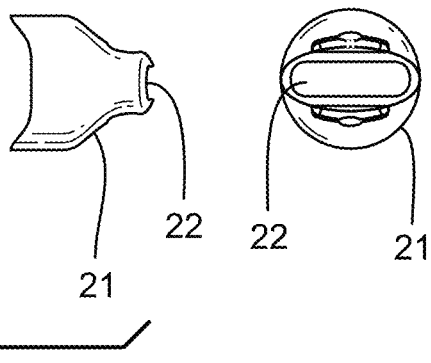
FIG. 22 is a fragmentary end view of a preferred embodiment of the apparatus of the present invention.
Figure 23:
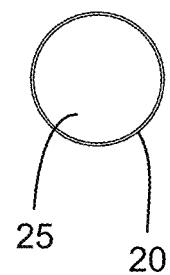
FIG. 23 is a fragmentary end view of the preferred embodiment of the apparatus of the present invention.
Figure 24:
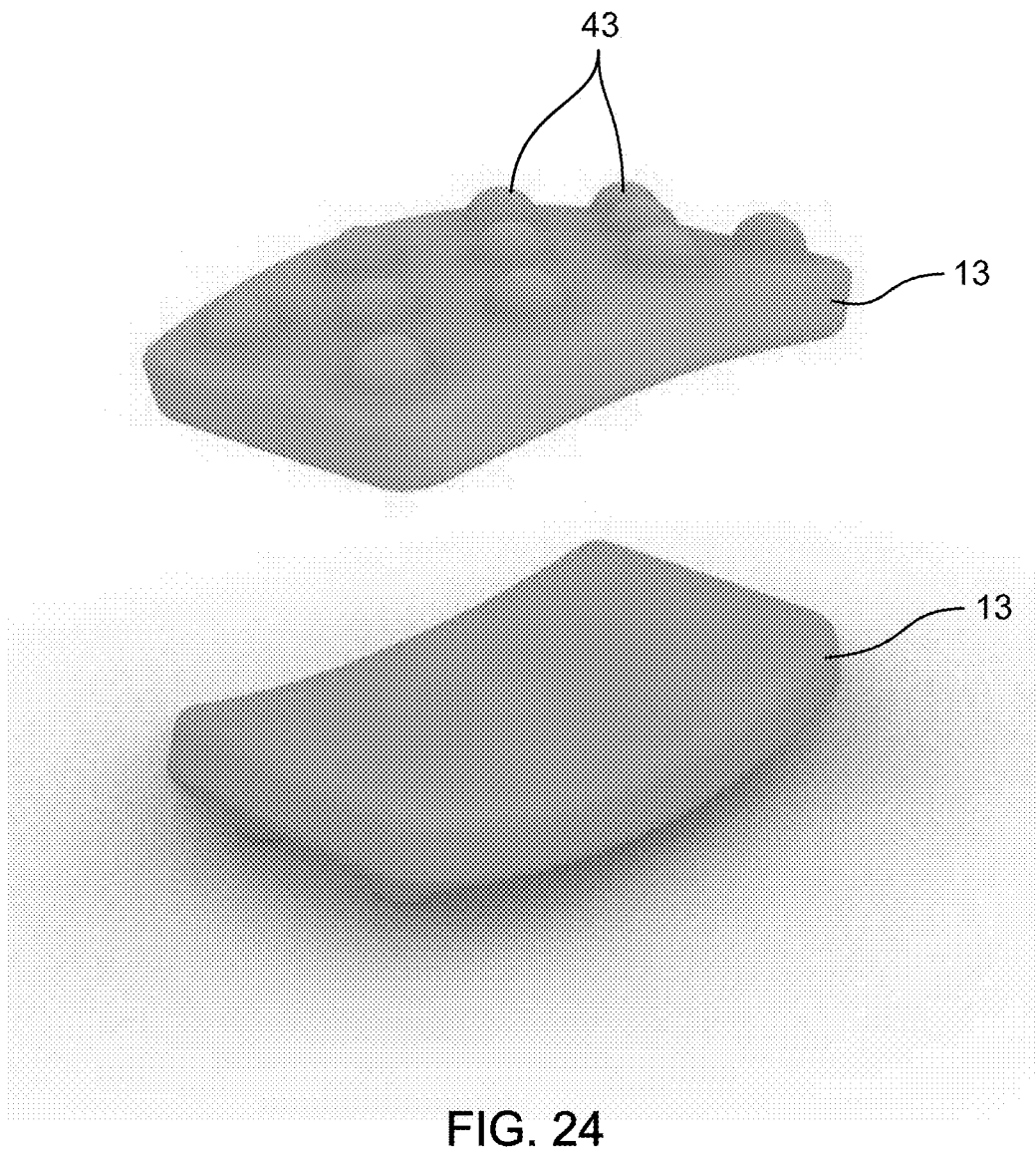
FIG. 24 is a fragmentary perspective view of a preferred embodiment of the apparatus of the present invention showing the candy inserts.
Figure 25:
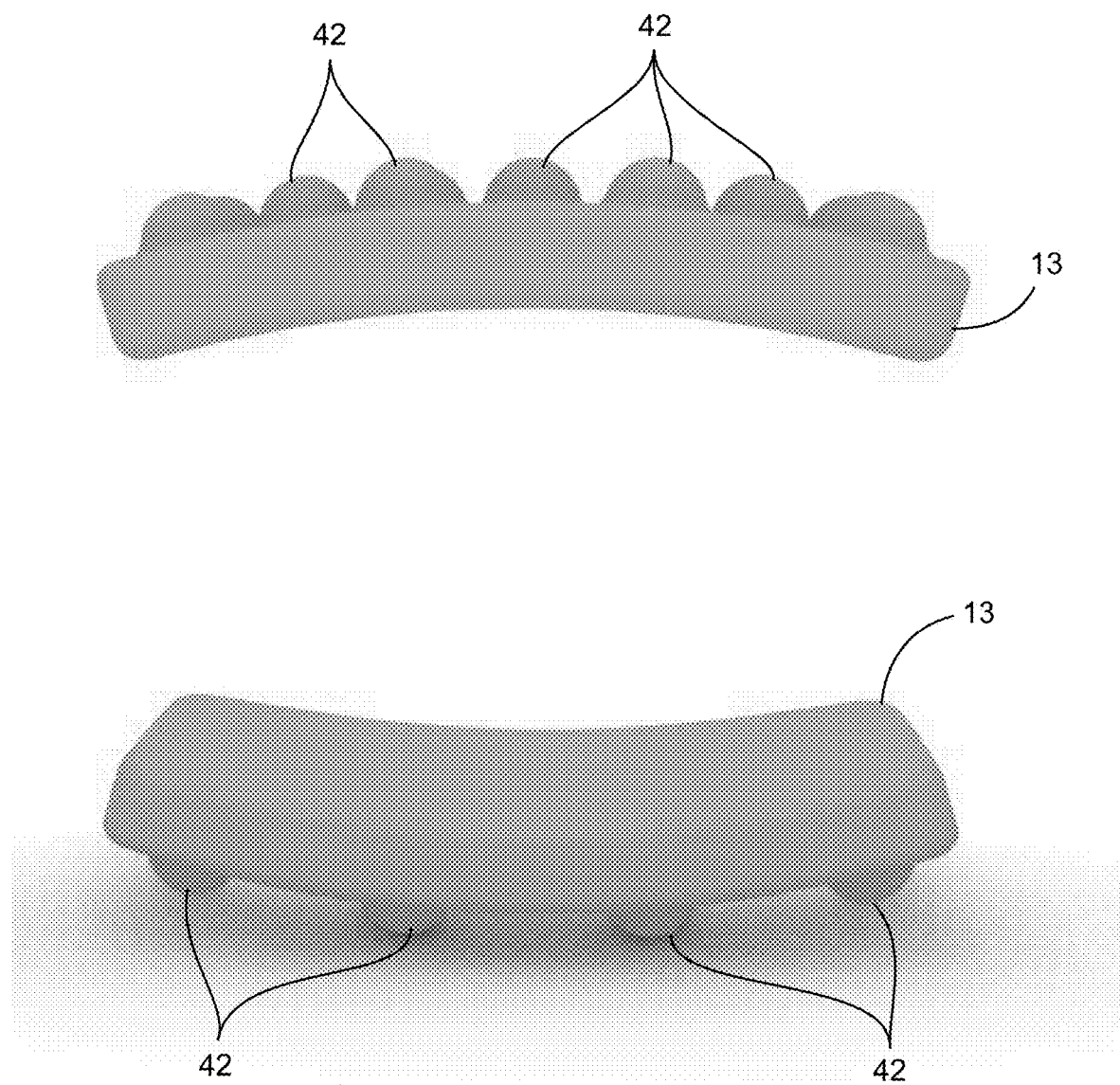
FIG. 25 is a fragmentary side view of a preferred embodiment of the apparatus of the present invention showing the candy inserts.
Figure 26:
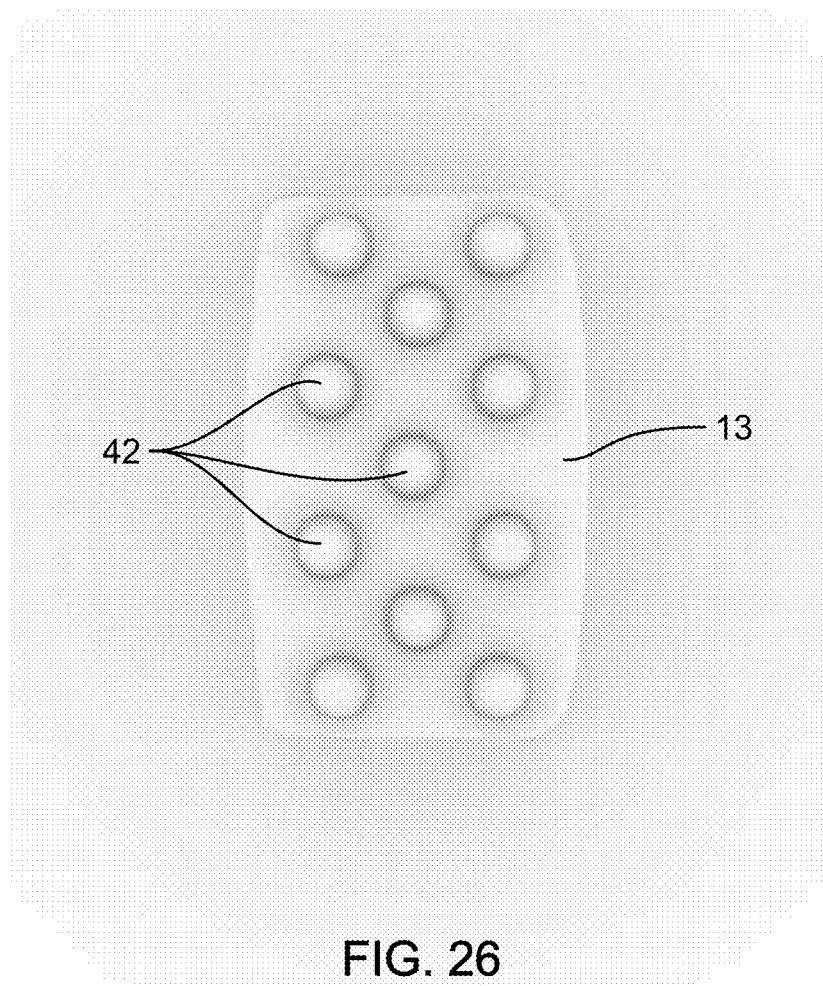
FIG. 26 is a fragmentary top view of a preferred embodiment of the apparatus of the present invention showing the candy insert.

FIGS. 2-17 show specially configured mouthpiece having mouthpiece body 20 having end portion 21 with opening 22 and end portion 23 having opening 24. An open-ended bore 25 connects opening 22 with opening 24. End portion 23 can connect with a nebulizer or nebulizer cup 11 (see FIG. 11). Body 20 can be a two-part body as seen in FIG. 18. Alternatively, body 20 and its components (including guard assemblies 26, 27, and candy inserts 13) can be a part of a nebulizer or nebulizer cup 11.

Figure 4:
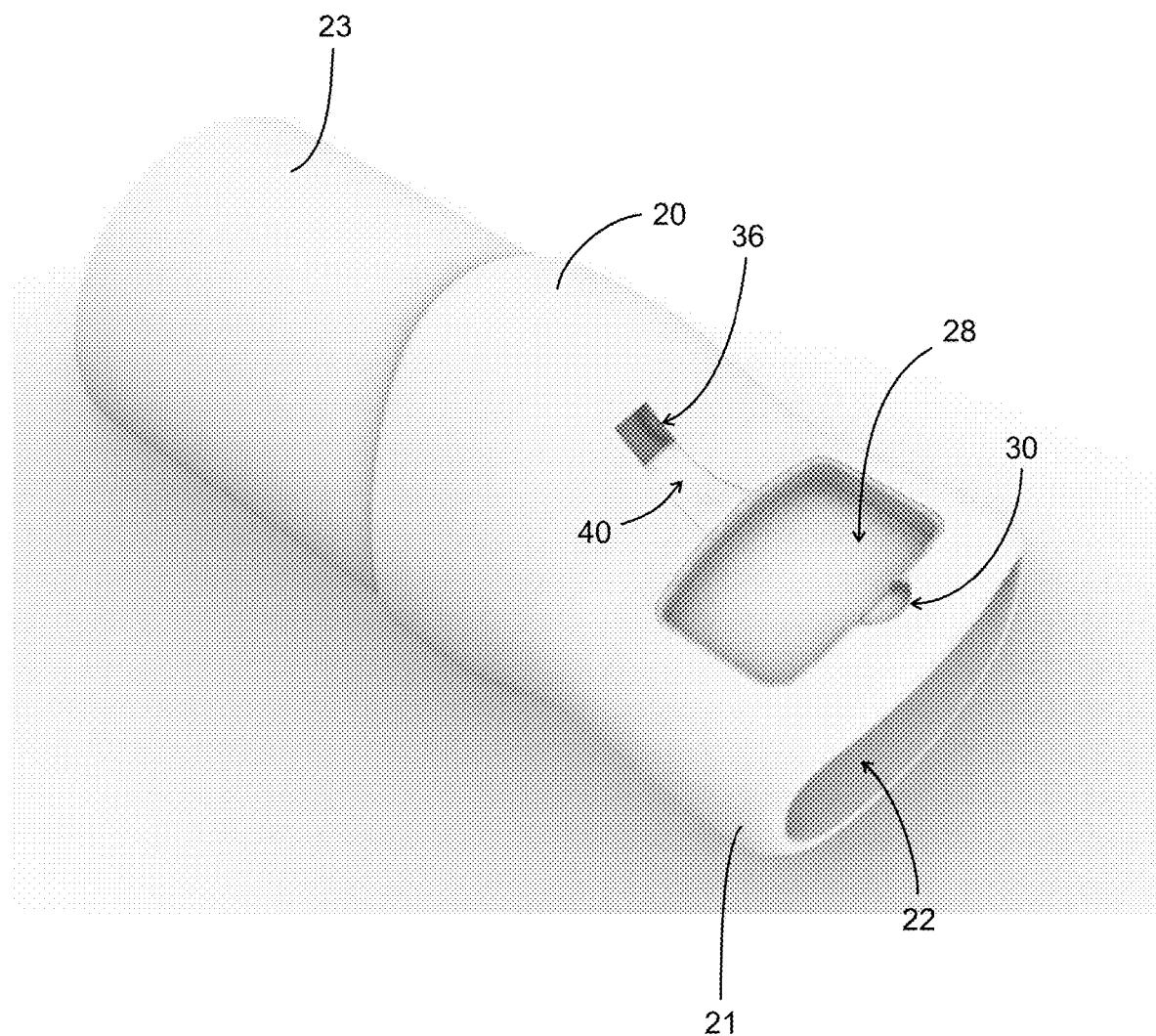
FIG. 4 is a side view of a preferred embodiment of the apparatus of the present invention with guard and candy insert removed.
Figure 13:
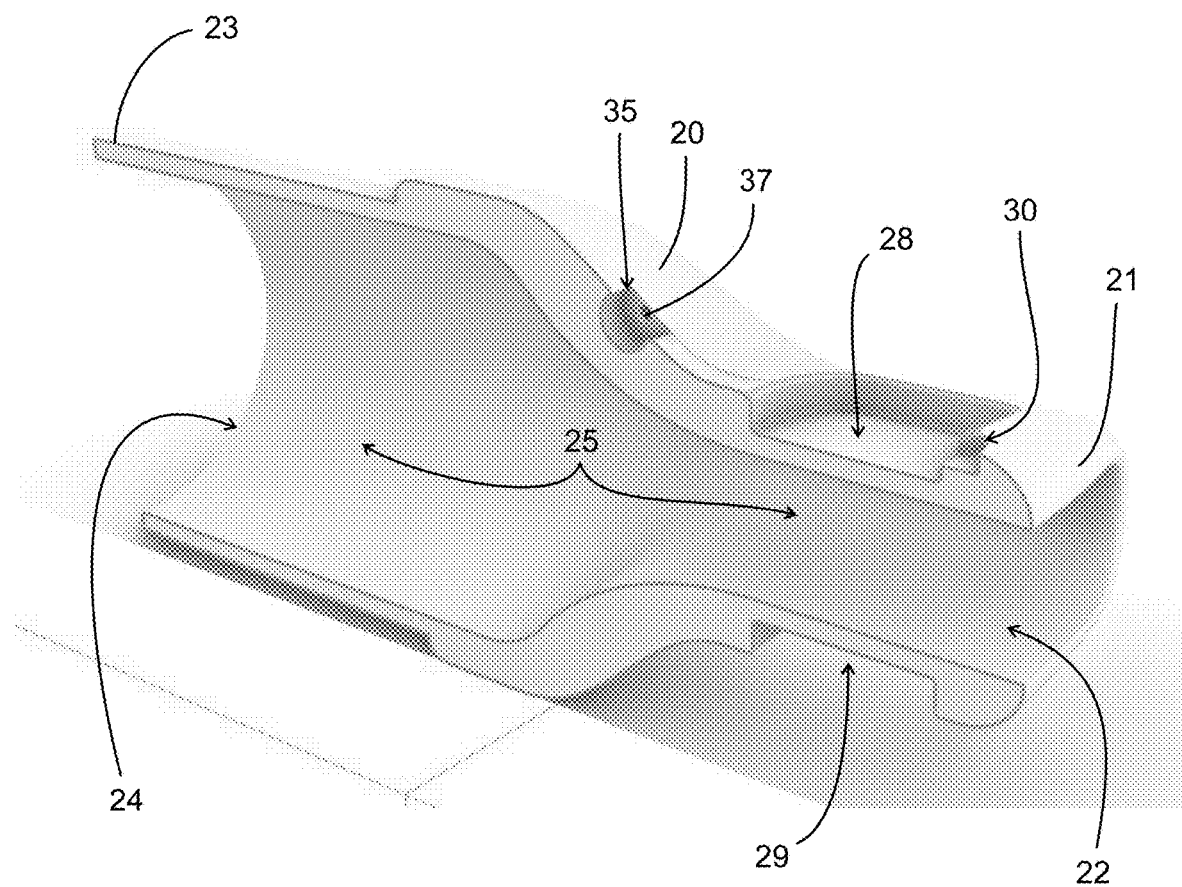
FIG. 13 is a partial sectional perspective view of a preferred embodiment of the apparatus of the present invention with candy insert removed.
Figure 14:
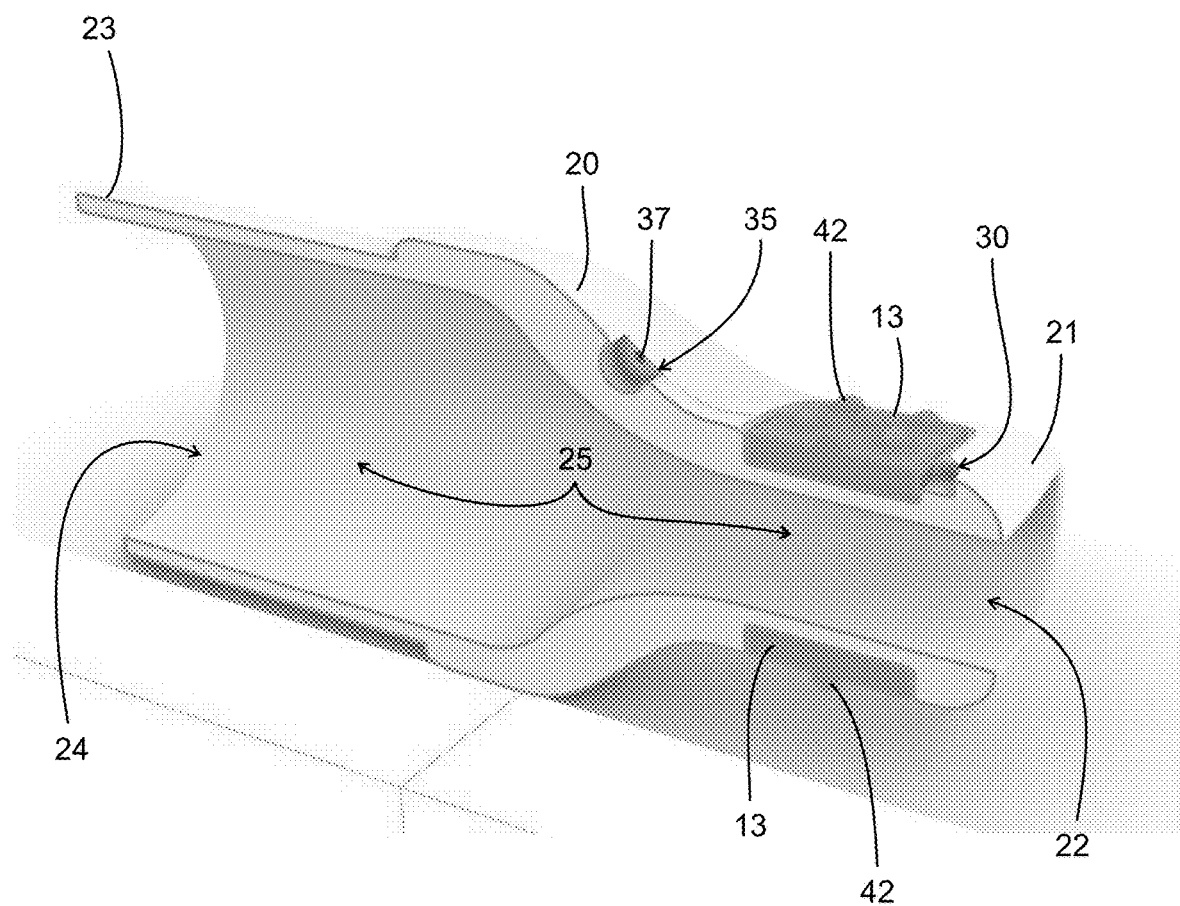
FIG. 14 is a partial sectional perspective view of a preferred embodiment of the apparatus of the present invention with guard removed.
Figure 15:
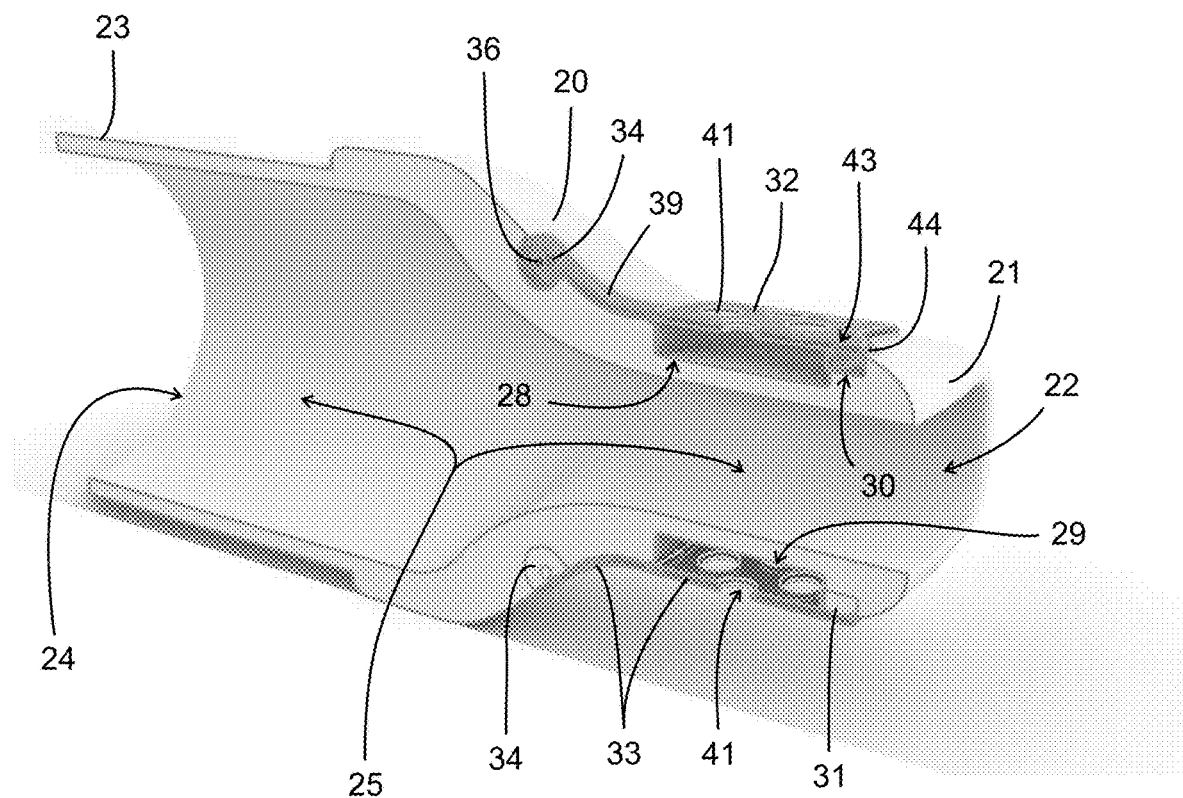
FIG. 15 is a partial sectional perspective view of a preferred embodiment of the apparatus of the present invention with candy insert removed and guards in closed position.
Figure 16:
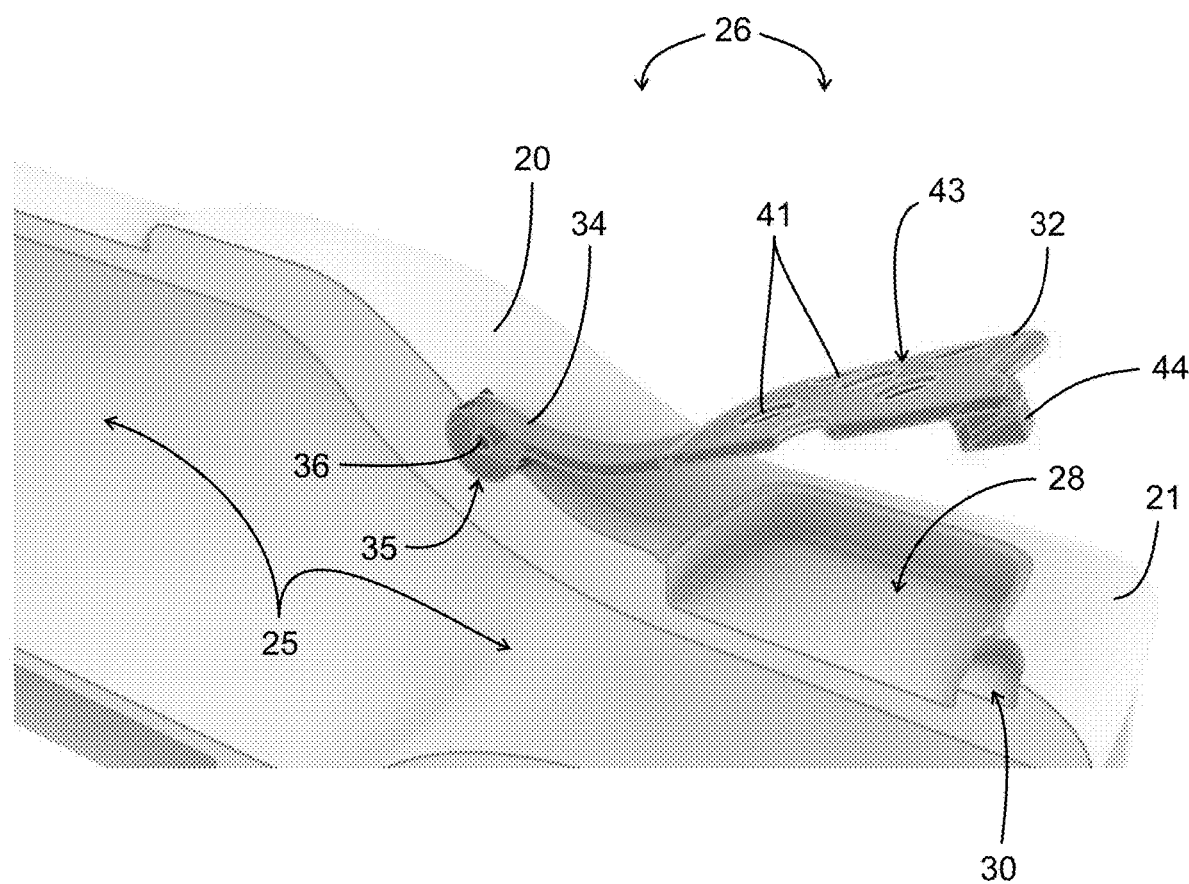
FIG. 16 is a perspective view of a preferred embodiment of the apparatus of the present invention with candy insert removed and guards in open position.
Figure 17:
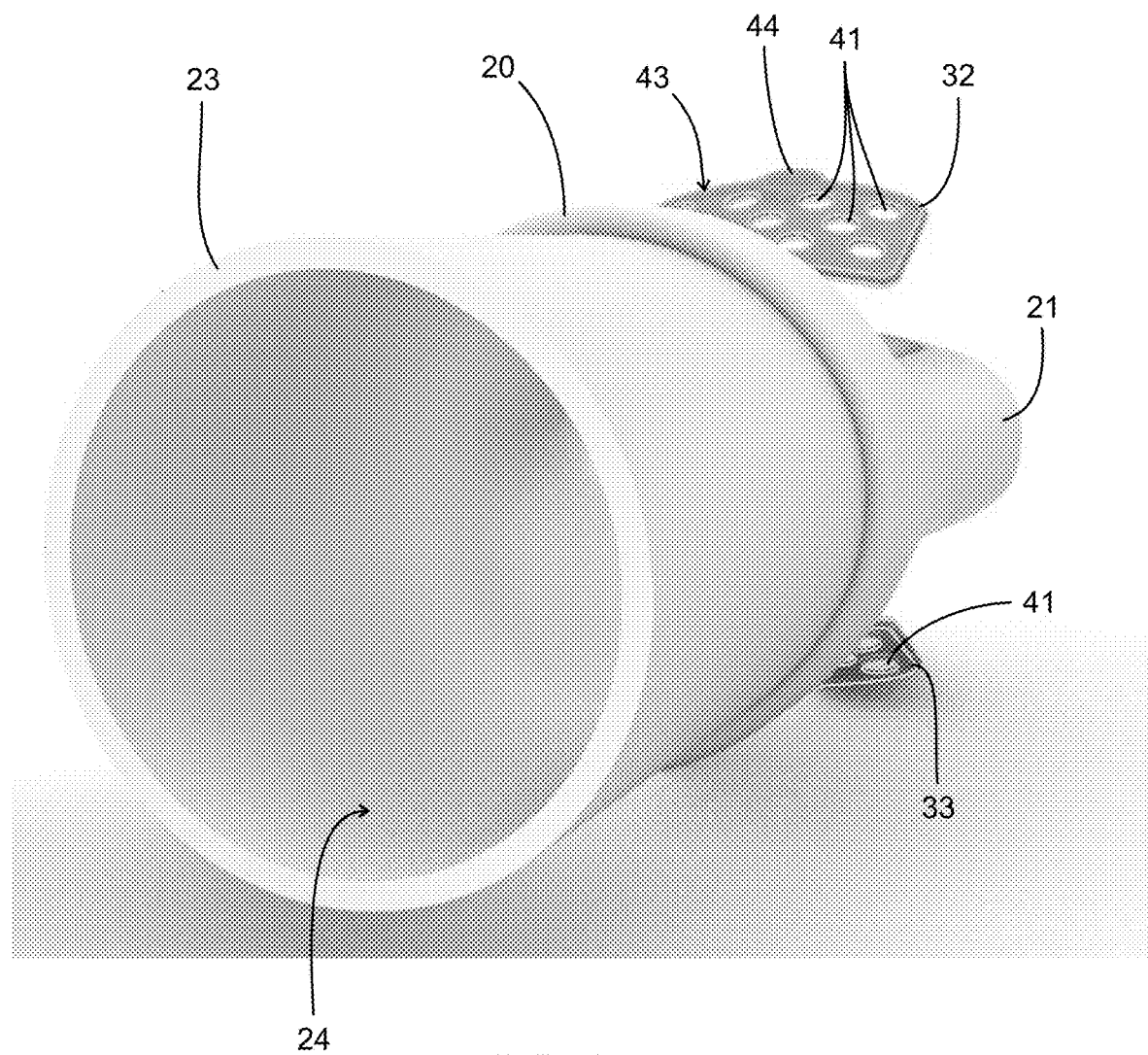
FIG. 17 is a perspective view of a preferred embodiment of the apparatus of the present invention with candy insert removed and guards in open position.

In FIGS. 4 and 13, body 20 has upper 28 and lower 29 recesses (e.g., rectangular or polygonal shape) each receptive of a candy insert 13. An arcuate or semicircular recess is provided next to each polygonal or rectangular recess 28, 29. Semicircular or arcuate recess 30 is next to recess 28. Semicircular or arcuate recess 31 is next to recess 29. Recesses 28, 29 can be of the same size and shape. Recesses 30, 31 can be of the same size and shape.

Each candy insert 13 fits into a recess 28 or 29 as seen in FIGS. 2, 3, 6, 7, 11 and 14. Upper and lower guards assemblies or safety nets 26, 27 are provided to prevent inadvertent removal of a candy insert 13 during use. These guard assemblies include upper candy holding guard 32 and lower candy holding guard 33 as seen in FIGS. 2, 5-8, 10, 11 and 15-17. Each guard assembly 26, 27 includes a hinge portion 34 that connects to body 20 at a hinge recess 36 via pin, pinned connection or pivot pin 36. Pin openings 37 in body 20 hold end portions of pin 36.

Each guard 32, 33 includes a rectangular portion 38 that is connected to hinge portion 34 with strap or arm 39. A recess 40 in body 20 is receptive of strap or arm 39. Rectangular portion 38 has openings 41 that are receptive of projections or bumps 42 on each insert 13 that project away from each candy insert 13 and away from body 20 as seen in FIGS. 2, 3, 5, 6, 7 and 11. Notice in FIGS. 2, 5 and 11 that the bumps or projections 42 extend above the outer surface 43 of each candy guard 32, 33. Preferably, these projections 42 extend approximately 2-3 mm above the base of the flavor attachment 13.

When a child user puts his or her mouth on end portion 21 of body 20, he or she will be able to taste the candy insert 13 projections 42. The bumps or projections can be sized to dissolve over a selected treatment time period such as 10-15 minutes (or more). Each guard 32, 33 has a tab 44 that enables dislocation of the guard 32 or 33 from body 20 such as when an insert 13 is to be removed and body 20 is to be cleaned.

Figure 2:
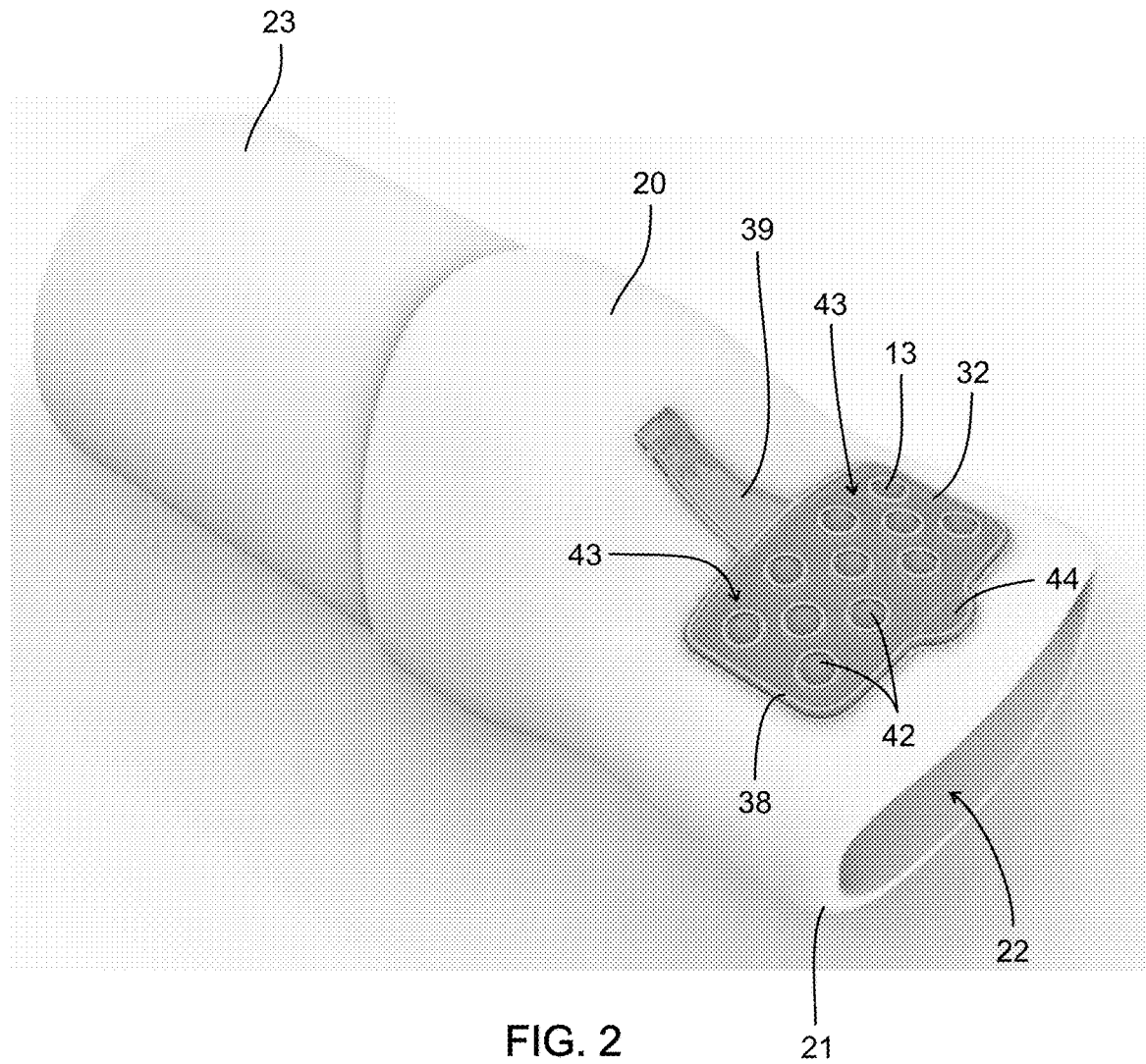
FIG. 2 is a perspective view of a preferred embodiment of the apparatus of the present invention with guard in closed position.
Figure 3:
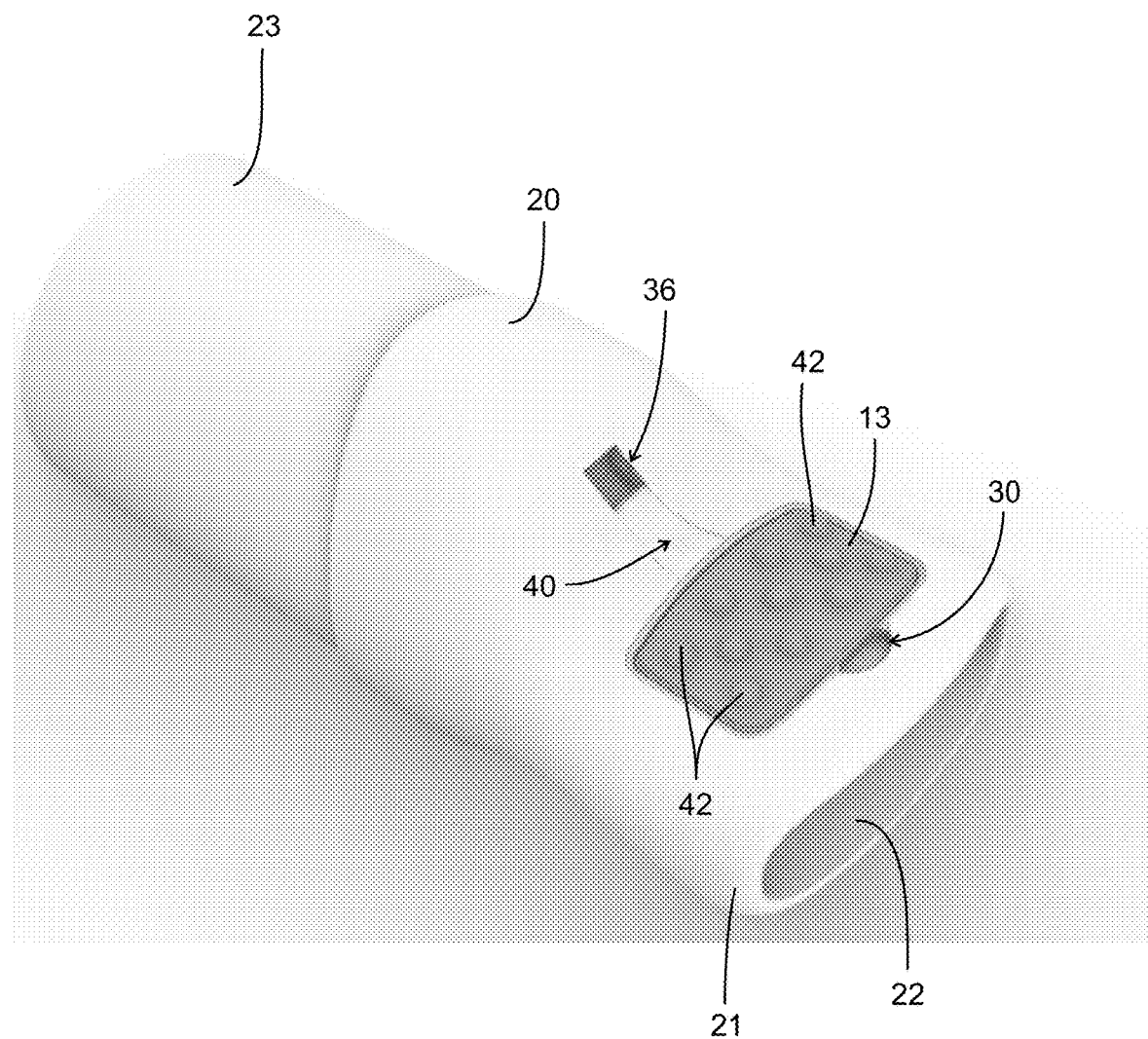
FIG. 3 is a perspective view of a preferred embodiment of the apparatus of the present invention with guard removed.
Figure 5:
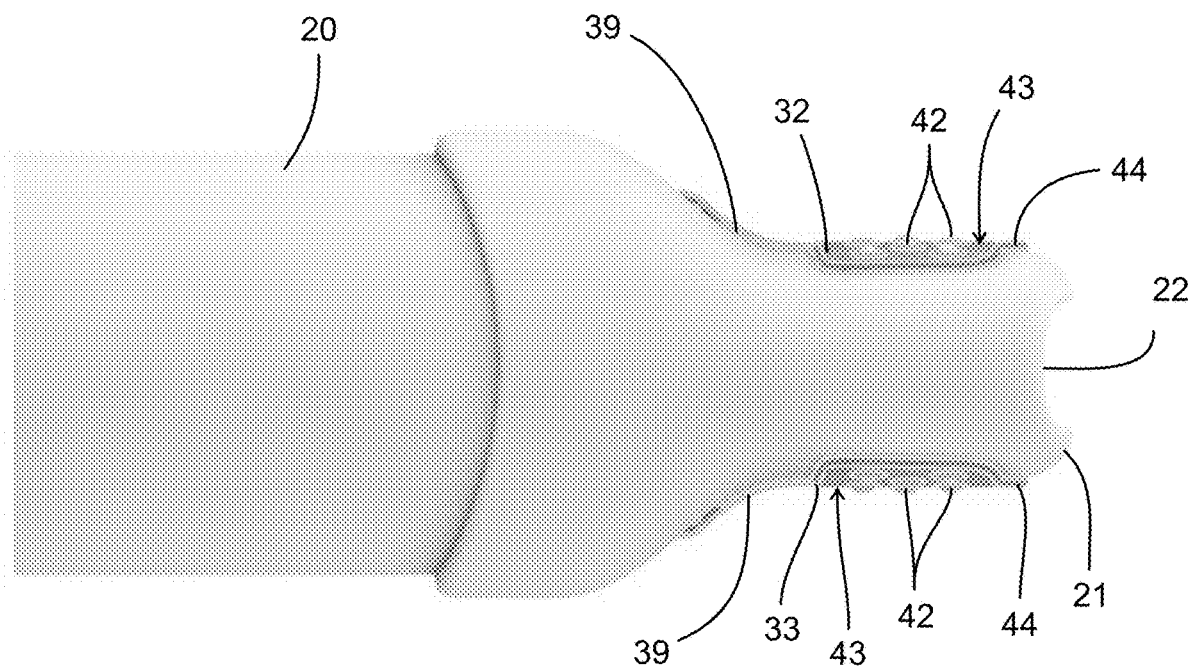
FIG. 5 is a side view of a preferred embodiment of the apparatus of the present invention with guard in closed position.
Figure 6:
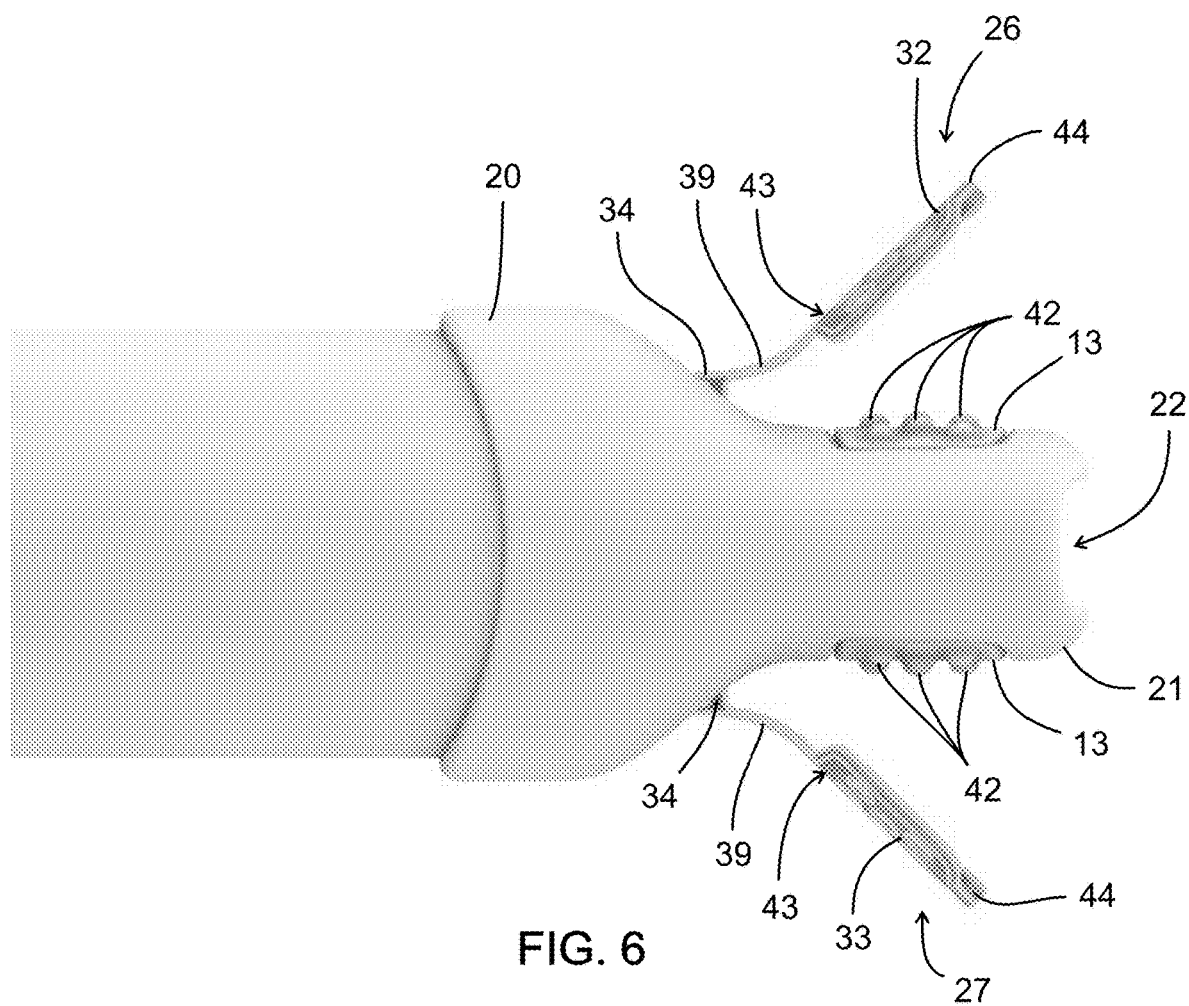
FIG. 6 is a side view of a preferred embodiment of the apparatus of the present invention with guards in open position.
Figure 7:
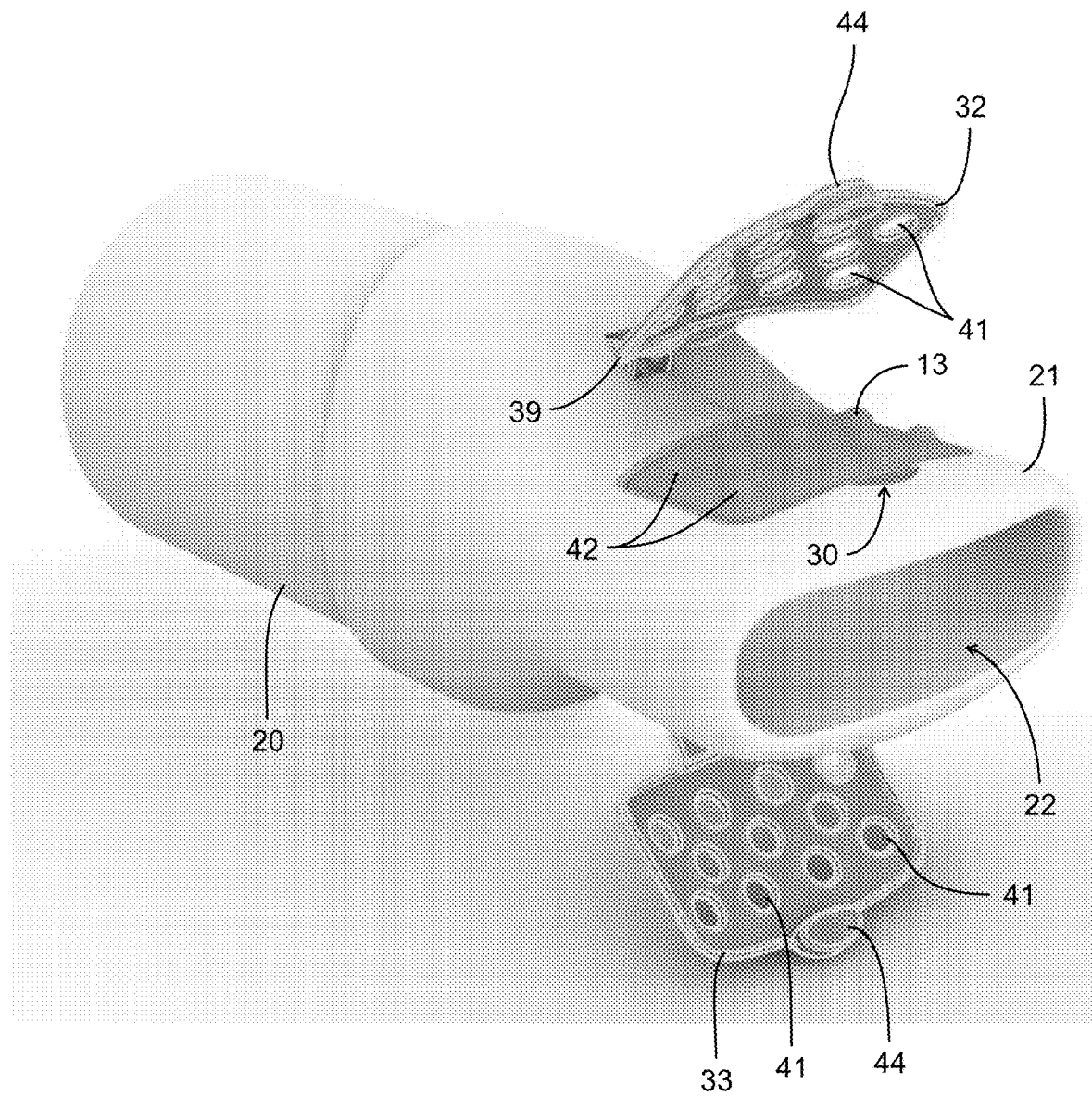
FIG. 7 is a perspective view of a preferred embodiment of the apparatus of the present invention with guards in an open position.
Figure 8:
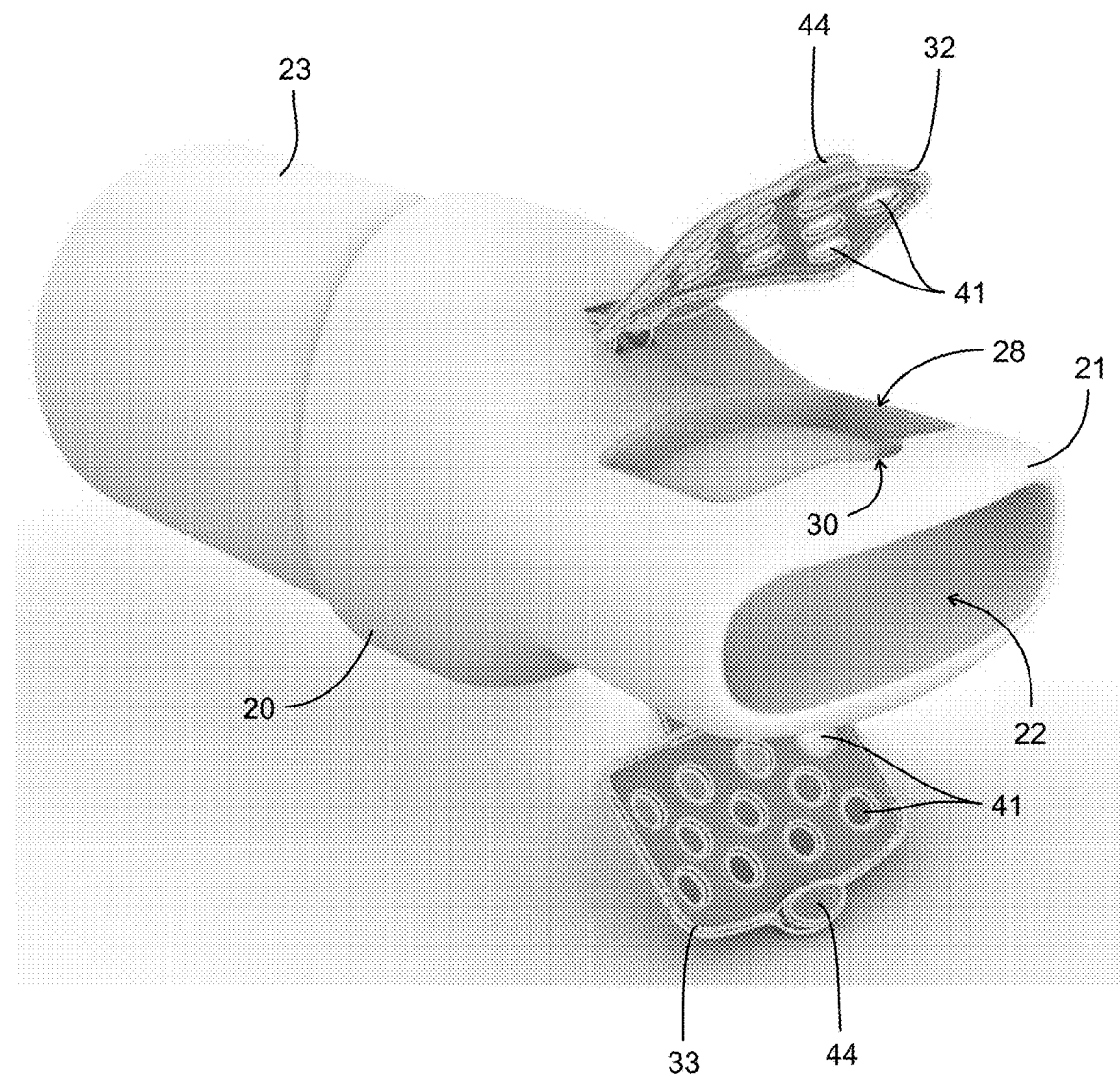
FIG. 8 is a perspective view of a preferred embodiment of the apparatus of the present invention with candy insert removed.
Figure 9:
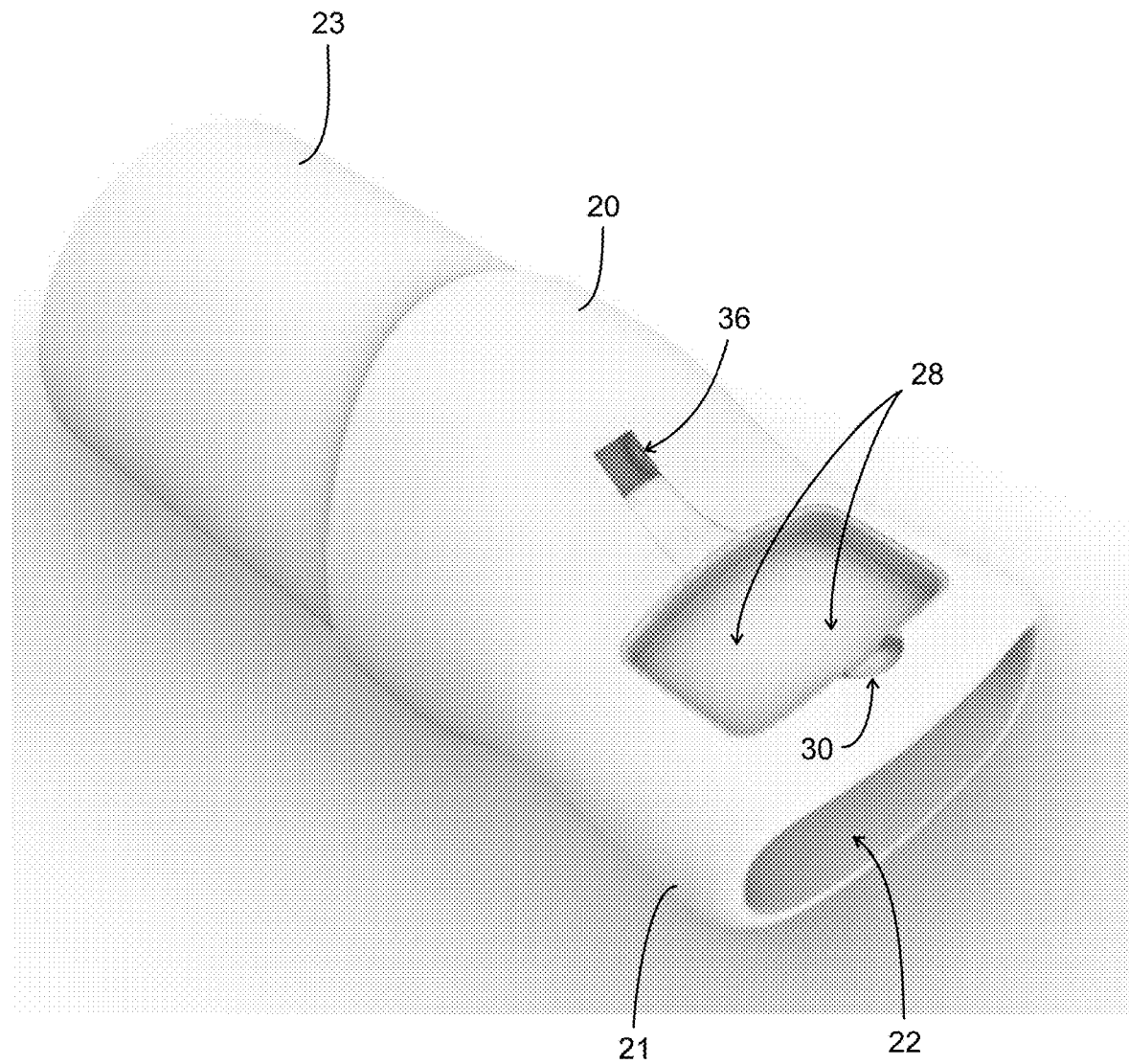
FIG. 9 is a perspective view of a preferred embodiment of the apparatus of the present invention with guard and candy insert removed.
Figure 10:
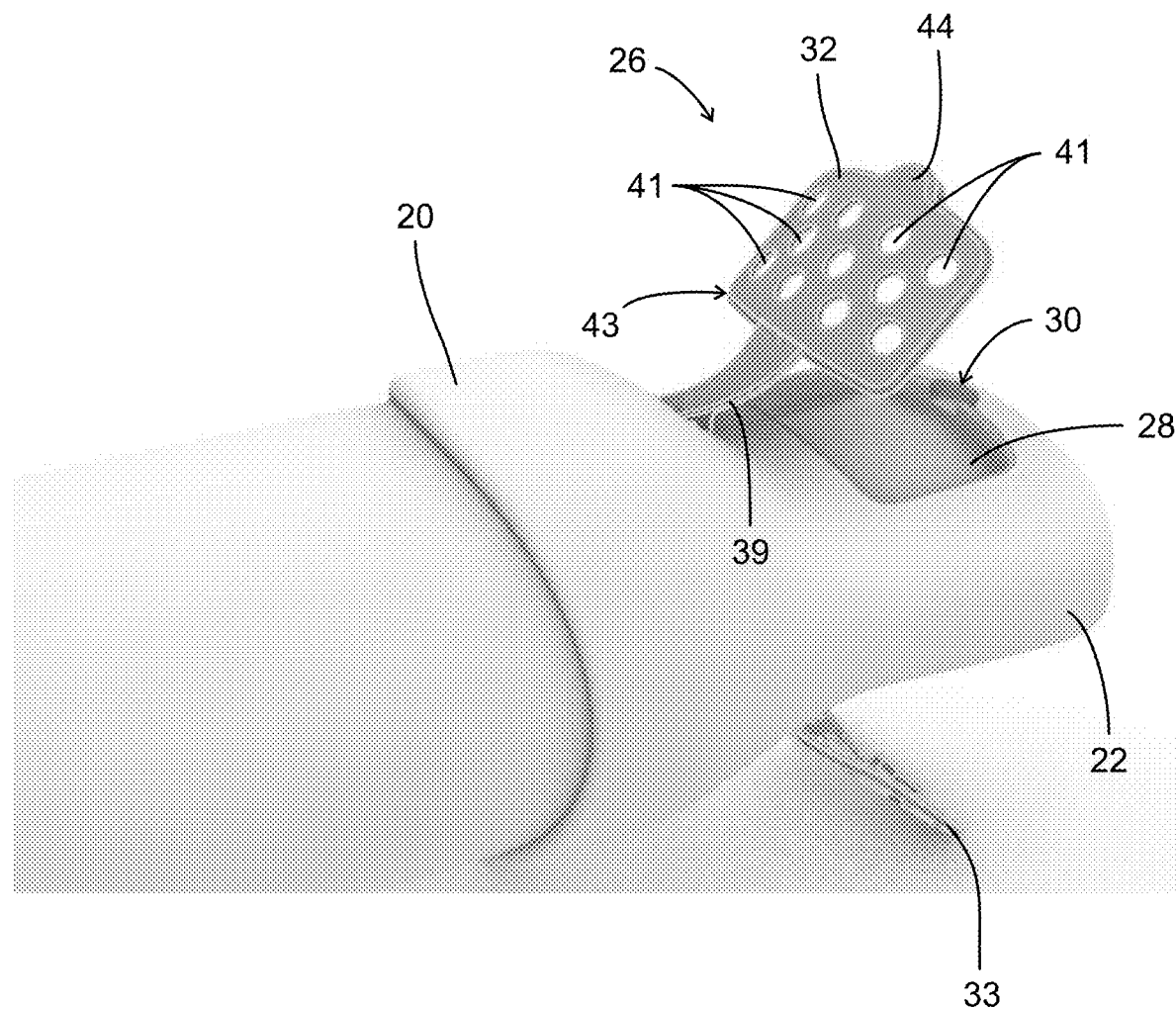
FIG. 10 is a perspective view of a preferred embodiment of the apparatus of the present invention with candy insert removed.
Figure 11:
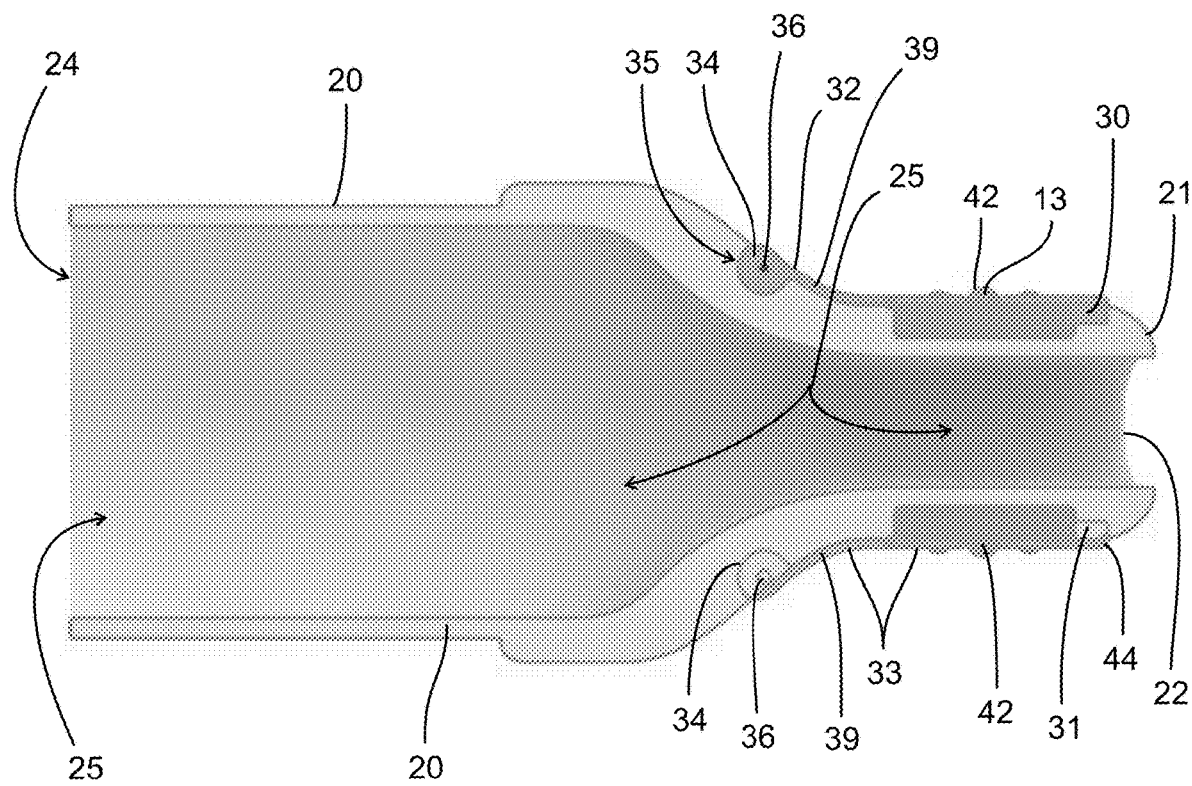
FIG. 11 is a sectional view of a preferred embodiment of the apparatus of the present invention.
Figure 12:
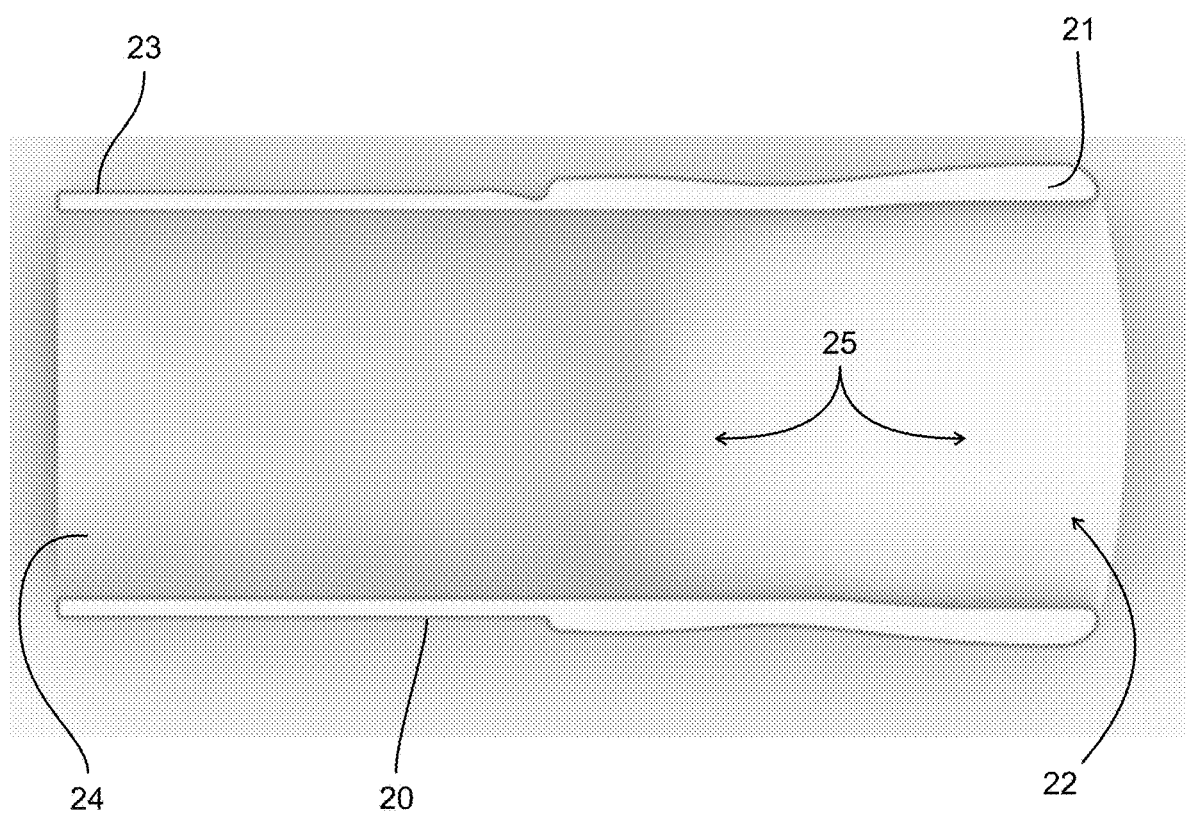
FIG. 12 is a partial sectional view of a preferred embodiment of the apparatus of the present invention.

Each tab 44 nests in a semicircular or arcuate recess 30 or 31. A user (parent or medical personnel) can remove the selected guard 32 or 33 thus pivoting arm or strap about pivot 36 to an open position (FIGS. 6-8, 10, and 16-17). The operational closed position is seen in FIGS. 2, 5 and 11.

The flavor attachment 13 is preferably sized and shaped to fit with a standard pediatric nebulizer cup or inhaler. For example, in some preferred embodiments, the attachment 13 is rectangular shaped having a length of approximately 16-17 mm and width of approximately 10-11 mm. Preferably, the rectangular attachment 13 can be curved to attach to the inhaler mouthpiece, causing the total height to be approximately 3.5-4.5 mm.

While the duration of treatment is typically interval of between about 1 and 20 minutes, in some children it could be hours, in which case an especially long-lasting candy or flavored substance could be used, or the candy or substance could be replaced as needed during the duration of treatment.

PARTS LIST

The following is a list of parts and materials suitable for use in the present invention:

| Parts Number | Description |
| --- | --- |
| 10 | respiratory therapy apparatus |
| 11 | nebulizer/nebulizer cup |
| 12 | mouthpiece |
| 13 | candy item/candy fitment/candy coating/candy layer/flavor attachment |
| 14 | child |
| 15 | compressor |
| 16 | tubing section |
| 20 | mouthpiece |
| 21 | end portion |
| 22 | opening |
| 23 | end portion |
| 24 | opening |
| 25 | flow bore |
| 26 | guard assembly |
| 27 | guard assembly |
| 28 | recess, rectangular recess |
| 29 | recess, rectangular recess |
| 30 | semicircular recess |
| 31 | semicircular recess |
| 32 | upper guard |
| 33 | lower guard |
| 34 | hinge portion |
| 35 | hinge recess |
| 36 | pivot pin, pinned connection |
| 37 | pin opening |
| 38 | rectangular portion |
| 39 | strap/arm |
| 40 | recess |
| 41 | opening |
| 42 | projection/bump |
| 43 | outer surface |
| 44 | tab |

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. A respiratory therapy inhaler apparatus, comprising:
 a) a compressor;
 b) a nebulizer configured to hold a selected pharmaceutical, said nebulizer having a mouthpiece with an opening that enables transmission of atomized particles of the pharmaceutical to a patient;
 c) tubing that connects the compressor to the nebulizer;

d) one or more recesses on the mouthpiece;

e) a candy article that occupies said one or more recesses, said candy article having one or more projecting portions;

f) a guard that covers said candy article, said guard having one or more open portions that enable said one or more projecting portions to extend beyond said guard so that a patient holding the mouthpiece in his or her mouth tastes the candy article; and g) wherein the one or more projecting portions dissolve over a selected time period that equates with a prescribed treatment duration wherein the patient retains the mouthpiece in his or her mouth.

2. The respiratory therapy inhaler apparatus of claim 1 wherein there are two recesses and two candy articles, each of said candy articles occupying a respective one of said recesses.

3. The respiratory therapy inhaler apparatus of claim 2 wherein the candy articles are spaced apart on said mouthpiece about 180 degrees apart.

4. The respiratory therapy inhaler apparatus of claim 1 wherein the guard is hingedly attached to the mouthpiece.

5. The respiratory therapy inhaler apparatus of claim 1 wherein said one or more projecting portions are arranged in rows and columns.

6. The respiratory therapy inhaler apparatus of claim 1 wherein there are multiple said projecting portions and said guard has multiple openings, one opening for each projecting portion.

7. The respiratory therapy inhaler apparatus of claim 1 wherein the guard has a thickness and each projecting portion has a height that is greater than said thickness.

8. The respiratory therapy inhaler apparatus of claim 1 wherein the pharmaceutical is albuterol.

9. The respiratory therapy inhaler apparatus of claim 1 wherein the pharmaceutical is budesonide.

* * * * *